US00PP08655P

United States Patent [19]

Cornelis

[11] Patent Number: Plant 8,655

[45] Date of Patent: Mar. 22, 1994

[54] SPATHIPHYLLUM PLANT NAMED DANIEL

[75] Inventor: Daniel Cornelis, Oosterzele, Belgium

[73] Assignee: Reginald Deroose, Evergem, Belgium

[21] Appl. No.: 974,172

[22] Filed: Nov. 10, 1992

[51] Int. Cl.[5] ..... A01H 5/00
[52] U.S. Cl. ..... Plt./88.1
[58] Field of Search ..... Plt. 88.1

*Primary Examiner*—James R. Feyrer
*Attorney, Agent, or Firm*—Foley & Lardner

[57] ABSTRACT

A new and distinct cultivar of Spathiphyllum plant named Daniel, characterized by its compact growth habit with excellent side shoot production, relatively large white flowers, particularly in relation to its compact growth, easy and frequent flowering, early flowering, and its toothed leaf margins.

1 Drawing Sheet

The present invention comprises a new and distinct cultivar of Spathiphyllum, botanically known as Spathiphyllum, and referred to by the cultivar name Daniel.

The new cultivar is a product of a planned breeding program, and was originated from a cross made by the inventor Daniel Cornelis in Melle, Belgium in 1988.

The male and female parents are unknown at this time. Both parents were seedling selections from a cross made by the inventor in Melle, Belgium between unidentified parents which were in turn seedlings obtained by mass selection from a cross made approximately twenty (20) years ago between Spathiphyllum 'Mona Loa' and an unnamed spathiphyllum walissii plant. Details of the parents and grandparents are not available.

Daniel was discovered and selected as a flowering plant within the progeny of the stated cross by the inventor in a controlled environment in Melle, Belgium. Subsequent asexual reproduction by the inventor in July 1988 in Evergem, Belgium by tissue culture has demonstrated that the combination of characteristics as herein disclosed for the new cultivar are firmly fixed and are retained through successive generations of asexual reproduction.

The following traits has been repeatedly observed and in combination distinguish Daniel as a new and distinct cultivar:

1. The new cultivar blooms relatively early, in 4 to 5 months starting from an acclimatized plantlet about 10 cm tall.
2. The cultivar produces large flowers (up to 15 cm high and 9 cm in width), particularly in comparison to the shape of the plant.
3. The leaves are slightly toothed at the margins.
4. Daniel flowers easily making the cultivar very floriferous.
5. The plant has a relatively short habit, extending no taller than 40 to 50 cm when flowering, but produces many side shoots thereby producing a well rounded plant.

The accompanying drawing comprises a color photograph showing a front perspective view of a typical plant of Daniel.

The following observations, measurements and values describe plants grown in Melle, Belgium under greenhouse conditions which closely approximate those generally used in horticultural practice. Color references are made to The Royal Horticultural Society (RHS) Colour Chart, except where general color terms or ordinary significance are used. The color values were determined between 9:00–10:00 a.m. on Mar. 28, 1990 under bright but slightly clouded daylight conditions at Melle, Belgium.

The new cultivar can be compared to the Spathiphyllum cultivar Adagio with respect to plant size and flower shape. Daniel is distinguished from Adagio by its larger leaves, greater number of flowers, easier, more frequent flowering, larger flowers relative to the size of the plant, and by its toothed leaf margin, as compared to the entire margin of Adagio.

Classification:
- *Botanical.*—Spathiphyllum cv. Daniel.
- *Commercial.*—Spathiphyllum.

Parentage:
- *Male parent.*—Unknown.
- *Female parent.*—Unknown.

Propagation: By tissue culture.

Plant: From 40 cm to 51 cm tall (above soil level and measured from bottom of the plant to the top of the tallest flower) when grown in 13 cm pots, and approximately 30 to 40 cm in diameter when fully grown.
- *Growth habit.*—Compact, full spreading by side shoots The plant produces about 3 to 4 side shoots.

Leaves:
- *Form.*—Elliptical, slightly asymmetrical acuminate base and tip. Leaf blade toothed in margin.
- *Size.*—Approximately 20 cm in length and 9 cm in width.
- *Texture.*—Leathery, upper surface glossy.
- *Veins.*—Weak to medium bulging between veins.
- *Color.*—Upper surface: Slightly darker than 137A. Lower surface: 137B.
- *Petioles.*—Length approximately 15–25 cm, diameter approximately 2–3.5 mm.; width of petiole wings approximately 0.5 cm, with the distance between the top of the wings and the base of the leaf being about 10 cm for the youngest leaves up to about 18 cm for older leaves.

Flowers:
- *Buds.*—Typical, in axils of the leaves. Spathe tightly rolled around spadix and extrudes from petiole sheath. Spathe is fully opened when pedicel is fully elongated.

Spathe:

*Size.*—Approximately 9 cm width and 15 cm in length.

*Color (RHS).*—White 155C-D with green midrib 143 A on outside; midrib on inside is 155 A.

*Arrangement.*—Single flower on straight, upright stem; approximately 18–26 cm in length measured from leaf sheath; the stem is at an angle of approximately 45° relative to the leaf base.

*Shape.*—Oval with curled acuminate apices, obtuse base symetrical.

*Flowering.*—First flower appears in 4 to 5 months (starting from 10 cm plantlet). The next flower appears approximately 6 weeks later. The plant is thereafter continuously flowering, normally having 3 to 5 flowers in bloom at one time.

Spadix:

*Size.*—5 to 6 cm long and 1 to 1.5 cm in diameter; cylindrical in shape.

*Color (RHS).*—158A-B.

*Longevity.*—Approximately 4 weeks.

*Arrangement.*—As spathe unrolls, immature spadix extends generally parallel to midrib of spathe. As spathe and spadix mature, spadix at its midpoint is spaced approximately 2–30 cm from spathe and extends from at an angle of approximately 30°–50° relative to the spathe midrib at the base of the spathe.

Reproductive organs:

*Anthers and filaments.*—White.

*Pistils.*—White, protruding between staminate flowers, firmly fixed to main axil.

*Stamens.*—White.

*Pollen.*—White.

Roots: White, fleshy main roots with fine lateral roots.

Disease resistance: No disease problems noted to date.

Fertility: The cultivar is not sterile but cannot be propagated true to form by seed.

I claim:

1. A new and distinct cultivar of Spathiphyllum plant named Daniel, as illustrated and described.

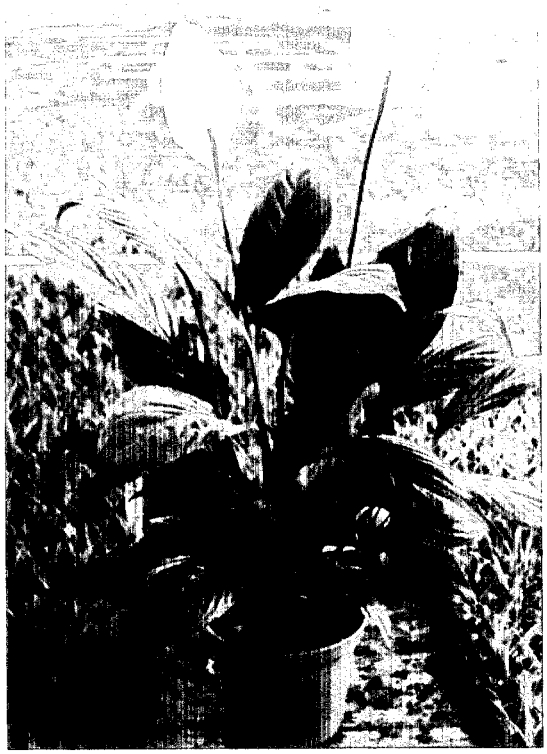

* * * * *